United States Patent
Yundt-Pacheco et al.

(10) Patent No.: US 10,161,947 B2
(45) Date of Patent: Dec. 25, 2018

(54) USING PATIENT RISK IN ANALYSIS OF QUALITY CONTROL STRATEGY FOR LAB RESULTS

(71) Applicant: Bio-Rad Laboratories, Inc., Hercules, CA (US)

(72) Inventors: John Christopher Yundt-Pacheco, Fairview, TX (US); Lakshmi Kuchipudi, Wylie, TX (US); Curtis Alan Parvin, McKinney, TX (US)

(73) Assignee: Bio-Rad Laboratories, Inc., Hercules, CA (US)

(*) Notice: Subject to any disclaimer, the term of this patent is extended or adjusted under 35 U.S.C. 154(b) by 662 days.

(21) Appl. No.: 14/702,019

(22) Filed: May 1, 2015

(65) Prior Publication Data
US 2016/0320420 A1 Nov. 3, 2016

(51) Int. Cl.
*G01N 35/00* (2006.01)
*G16H 50/30* (2018.01)
*G06F 19/00* (2018.01)

(52) U.S. Cl.
CPC ....... *G01N 35/00623* (2013.01); *G06F 19/00* (2013.01); *G16H 50/30* (2018.01); *G06F 19/36* (2013.01)

(58) Field of Classification Search
None
See application file for complete search history.

(56) References Cited

U.S. PATENT DOCUMENTS

| | | | |
|---|---|---|---|
| 5,937,364 A | 8/1999 | Westgard et al. |
| 6,556,951 B1 | 4/2003 | Deleo et al. |
| 7,050,933 B2 | 5/2006 | Parvin et al. |
| 2003/0101012 A1 | 5/2003 | Parvin et al. |
| 2010/0145630 A1 | 6/2010 | Ball et al. |
| 2010/0295685 A1 | 11/2010 | Parvin et al. |

OTHER PUBLICATIONS

Westgard, James, O., et al., "Design and Evaluation of Statistical Control Procedures: Applications of a Computer 'Quality Control Simulator' Program," Clinical Chemistry, 1981, vol. 27, No. 9, pp. 1536-1545.

(Continued)

*Primary Examiner* — Larry D Riggs, II
(74) *Attorney, Agent, or Firm* — Kilpatrick Townsend & Stockton LLP

(57) ABSTRACT

Methods, apparatuses, and systems are disclosed for analyzing quality control (QC) strategies that are applied to testing processes an analyte in order to meet an acceptable level of probability of patient harm that could result from incorrect test results. The measure of patient harm takes into account severity of patient harm, as well as its occurrence. Methods include calculating, based on the parameters of the QC strategies and the test apparatus, an expected number of incorrect final results $E(N_{uf})$ due to a test system failure. The value of $E(N_{uf})$ can be used as part of a calculation of a predicted level of probability patient harm. The ratio of the acceptable level of probability of patient harm to the predicted level of probability patient harm can determine the adequacy of the QC strategies.

26 Claims, 12 Drawing Sheets

(56) References Cited

OTHER PUBLICATIONS

Dechert, Jerry, et al., "Multivariate approach to quality control in clinical chemistry," Clinical Chemistry, 1998, vol. 44, No. 9, pp. 1959-1963.
International Search Report and Written Opinion dated Sep. 18, 2012, PCT/US12/43582, 8 pages.
Parvin, Curtis, A., "Assessing the Impact of the Frequency of Quality Control Testing on the Quality of Reported Patient Results," Clinical Chemistry, 2008, vol. 54, No. 12, pp. 2049-2054.
Parvin, Curtis, A., "New Insight into the Comparative Power of Quality-Control Rules that Use Control Observations within a Single Analytical Run," Clinical Chemistry, 1993, vol. 39, No. 3, pp. 440-447.

| 300 Probability of Harm | Severity of Harm | | | | |
|---|---|---|---|---|---|
| | Negligible | Minor | Serious | Critical | Catastrophic |
| Frequent | Unacceptable | Unacceptable | Unacceptable | Unacceptable | Unacceptable |
| Probable | Acceptable | Unacceptable | Unacceptable | Unacceptable | Unacceptable |
| Occasional | Acceptable | Acceptable | Acceptable | Unacceptable | Unacceptable |
| Remote | Acceptable | Acceptable | Acceptable | Acceptable | Unacceptable |
| Improbable | Acceptable | Acceptable | Acceptable | Acceptable | Acceptable |

FIG. 3

Probability of Harm Categories

| Category Level | CLSI EP23 Example | ISO 14971 Example |
|---|---|---|
| Frequent | Once/week | ≥1/1,000 |
| Probable | Once/month | <1/1,000 and ≥1/10,000 |
| Occasional | Once/year | <1/10,000 and ≥1/100,000 |
| Remote | Once/few years | <1/100,000 and ≥1/1,000,000 |
| Improbable | Once/life of measuring system | <1/1,000,000 |

USING PATIENT RISK IN ANALYSIS OF QUALITY CONTROL STRATEGY FOR LAB RESULTS

CROSS-REFERENCES TO RELATED APPLICATIONS

This application is related to commonly owned U.S. Pat. No. 8,738,548 entitled "System And Method For Determining An Optimum QC Strategy For Immediate Release Results" by Parvin and Yundt-Pacheco, the disclosure of which is incorporated by reference in its entirety.

BACKGROUND

Diagnostic devices are used for a number of purposes in medicine, research, and other industries. For example in medicine, a diagnostic device may be used to measure the concentration of a particular substance (analyte) in a blood or urine specimen. It is important to ensure that the diagnostic device operates properly and that the test results returned are correct. In particular, it is important to ensure that the device is not operating with a systematic error that can corrupt a large portion of results produced.

When a sample is tested for the analyte, the instrument will return a test result, which may differ from the physically correct value. It is typically the case that test results provided by measuring devices have an inherent imprecision, that is, a predetermined range or margin of error. A test result may be deemed to be acceptable if the difference between the device's reported result and the correct value is within the inherent imprecision.

Since during use there often is no way to know the correct value of the specimens submitted for testing, the equipment may be periodically tested with reference samples to detect incorrectly reported results and systematic errors. In order to test the equipment, an operator may test one or more reference samples for which the correct result is known. Whereas a patient specimen may only be stable for a number of hours or days after collection, a reference sample may be a synthetic sample designed to be stable and testable for a much longer period of time, such as a number of months or years.

Once the testing values for the reference samples are obtained, they may be verified against a set of predetermined Quality Control ("QC") criteria. Conducting this procedure, whether one or more samples are tested, may be referred to as a QC event. When more than one sample is tested, one sample with a corresponding normal value, one with an abnormally high value and one with an abnormally low may be tested to ensure that equipment returns correct results across the entire scale of results. Furthermore, a number of samples with the same value may be tested to ensure that the equipment consistently returns the same results.

If the results meet the QC criteria, the equipment is determined to be returning good results and accordingly not subject to any systematic errors, and it can be used to test further patient specimens. If the results do not meet the prescribed criteria, the equipment is likely to have started malfunctioning at some point before or during the QC event. The malfunctioning may have started after testing the last patient specimen, but before the QC event, in which case all the patient results will have been reported correctly. On the converse the error can have occurred at any point in time before the QC event, and all the results reported for the patient specimens tested following such failure may have been reported with an error greater than the acceptable margin of error.

If patient results obtained after a successful QC event are not released until the following QC event has been passed, the number of reported errors can be greatly reduced. The need for immediate release of test results often renders this option impractical, and another solution is therefore needed.

The operator can in general decrease the expected number of incorrectly reported patient results by increasing the number of QC events and by testing more reference samples at each QC event. However, increasing either of these increases cost and decreases the number of patient specimens that can be tested by the equipment during any period of time.

BRIEF SUMMARY

Methods and systems are disclosed for analyzing a quality control (QC) strategy, e.g., for measurements of a particular analyte in patient specimens using a particular instrument. The analysis may use patient risk. For example, the analysis can use both a probability and severity of patient harm in providing an assessment of the QC strategy. A QC strategy can include an interval between QC events that monitor the particular instrument using reference samples, and the number of reference samples tested at each quality control event.

Embodiments can obtain as inputs: a non-failure probability of incorrectly reported (incorrect) patient results $P_E(0)$ of a particular test instrument for a particular analyte; an average number of patient results reported between failures of the particular instrument; and a probability $P_{h|u}$ that an unreliable (incorrect) patient result leads to patient harm. An expected number of unreliable final results $E(N_{uf})$ for a QC strategy can be calculated. An assessment of the predicted probability of harm compared to an acceptable probability of harm can be provided. The acceptable probability of harm is dependent on the severity of harm resulting from an incorrectly reported patient result.

Other embodiments are directed to systems, portable consumer devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 3 shows a risk acceptability matrix according to embodiments.

FIG. 4 shows a probability of harm table according to embodiments.

DETAILED DESCRIPTION

In addition to reducing the number of incorrectly reported patient results, another factor to be considered is the potential for patient risk if incorrect test results are used in diagnosis or determining treatment. Patient risk depends on both the severity of harm to the patient and the probability of the harm. The severity of the harm to a patient from an inappropriate medical decision or action based on incorrect test results can vary from negligible (e.g., mild discomfort) to catastrophic (e.g., hospitalization or death). In addition to severity of harm, the probability of such incorrect test results leading to patient harm can be accounted for in analyzing a QC strategy. For example, incorrect tests result leading only to treatments causing negligible harm can be tolerated with a probability of occurrence higher than for incorrect treatments that lead to serious harm.

Methods and systems are described for reducing risks of patient harm arising from incorrect test system results, which can lead to inappropriate treatments or lack of treatments. Various embodiments take into account the level of harm that can occur and the probability of such harm. Embodiments can use parameters of a Quality Control (QC) strategy to calculate a probability of harm. That calculated probability of harm can then be compared to an acceptable probability of harm, which can be based on appropriate standards. The parameters of the QC strategy can then be modified if necessary.

I. Events Leading to Harm

Various events may lead to a patient being harmed. Such events can include a device being inaccurate, which can then lead to a misdiagnosis, and the patient being harmed. Below is an example sequence of events.

Figure 1:
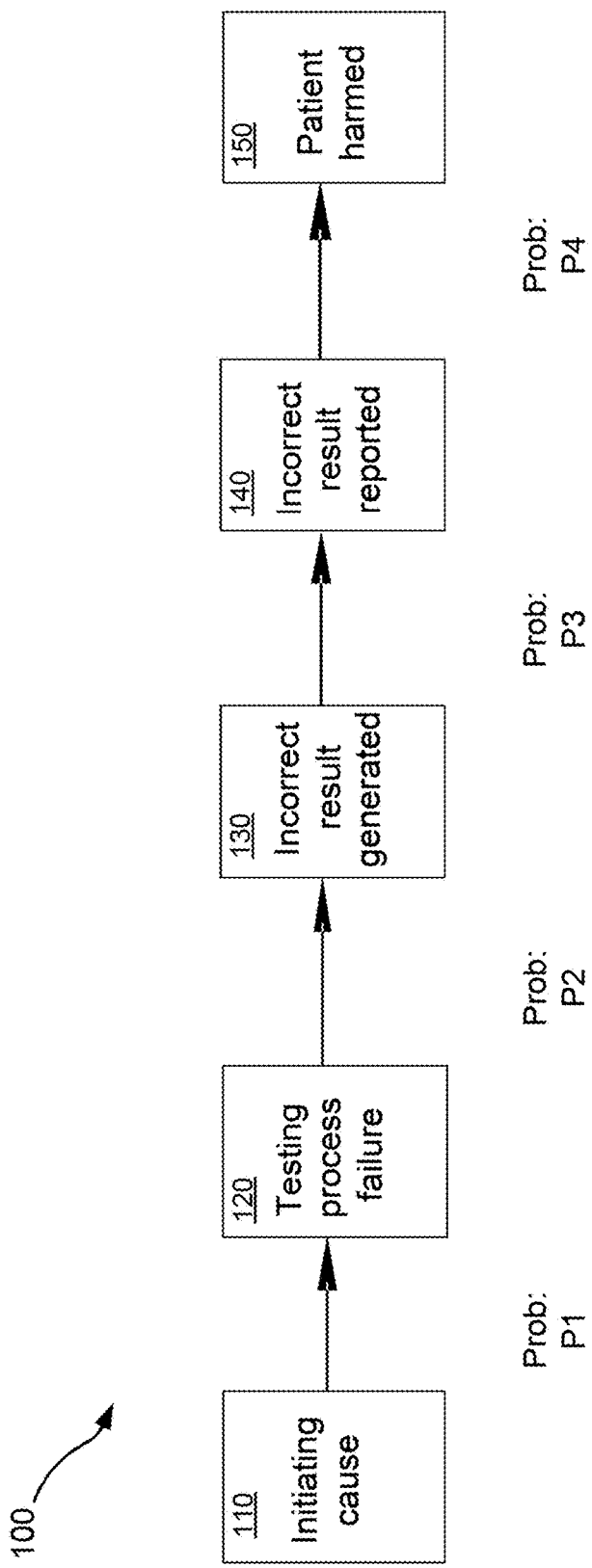
FIG. 1 shows a sequence of events that could occur in testing specimens and produce patient harm.

FIG. 1 shows a sequence 100 of events that could occur in testing specimens and produce patient harm. Sequence 100 may occur in a testing laboratory using a diagnostic device to provide test results for an analyte. The description that follows uses the example of a QC strategy adopted for a particular test instrument that measures a particular analyte. Example analytes include a blood glucose level, blood cholesterol level, and urine sugar level.

At event 110, an initiating cause produces a testing process failure, such as drift of measurement accuracy within the instrument, partial failure of the instrument, or incorrect operator input. The initiating cause may introduce a systematic error in the device's test results that is distinct from the device's inherent imprecision. In some cases, such an initiating cause may be immediately detected, such as by self-diagnostic components of the device itself, or by operator detection. However, the initiating cause may not be immediately detected, leading to a failure of the testing process. The probability of such an initiating cause producing a testing process failure that is not immediately detected, P1, can be estimated based on operator experience and known properties of the device.

At event 120, an undetected failure of the testing process can lead to an incorrect patient result being generated. There is a probability P2 that the testing process failure 120 leads to an incorrect patient result being generated. The probability P2 can depend on the acceptable measurement error level for the analyte and the QC strategy.

At event 130, an incorrect test result is reported to medical care providers with probability P3. The probability P3 can be determined in part by the QC strategy. For example, how rapidly the initiating cause is detected by QC events limits the probability that an undetected incorrect undetected result is reported to medical care providers.

Thereafter, at event 140, the incorrect result could lead to an inappropriate medical action causing patient harm, 150, with probability P4. This is an outcome that QC strategies are designed to reduce.

II. QC Design

A QC strategy can be designed to provide certain goals. A QC strategy can include an interval between QC events that monitor the particular instrument using a reference sample and a number of reference samples tested at each quality control event. These values can be adjusted to achieve a goal.

A. Overview

It is the goal of a QC strategy to reduce, where possible, each of the probabilities in the event sequence of FIG. 1. The testing system and its QC strategy can influence stages 110 to 140. A QC strategy typically involves placement of an instrument monitoring QC events on the instrument, i.e., how many in-use patient diagnostic tests are performed by the instrument between QC events. The following now explains how this, and other factors, can influence the chance of incorrect test results being reported.

Figure 2:
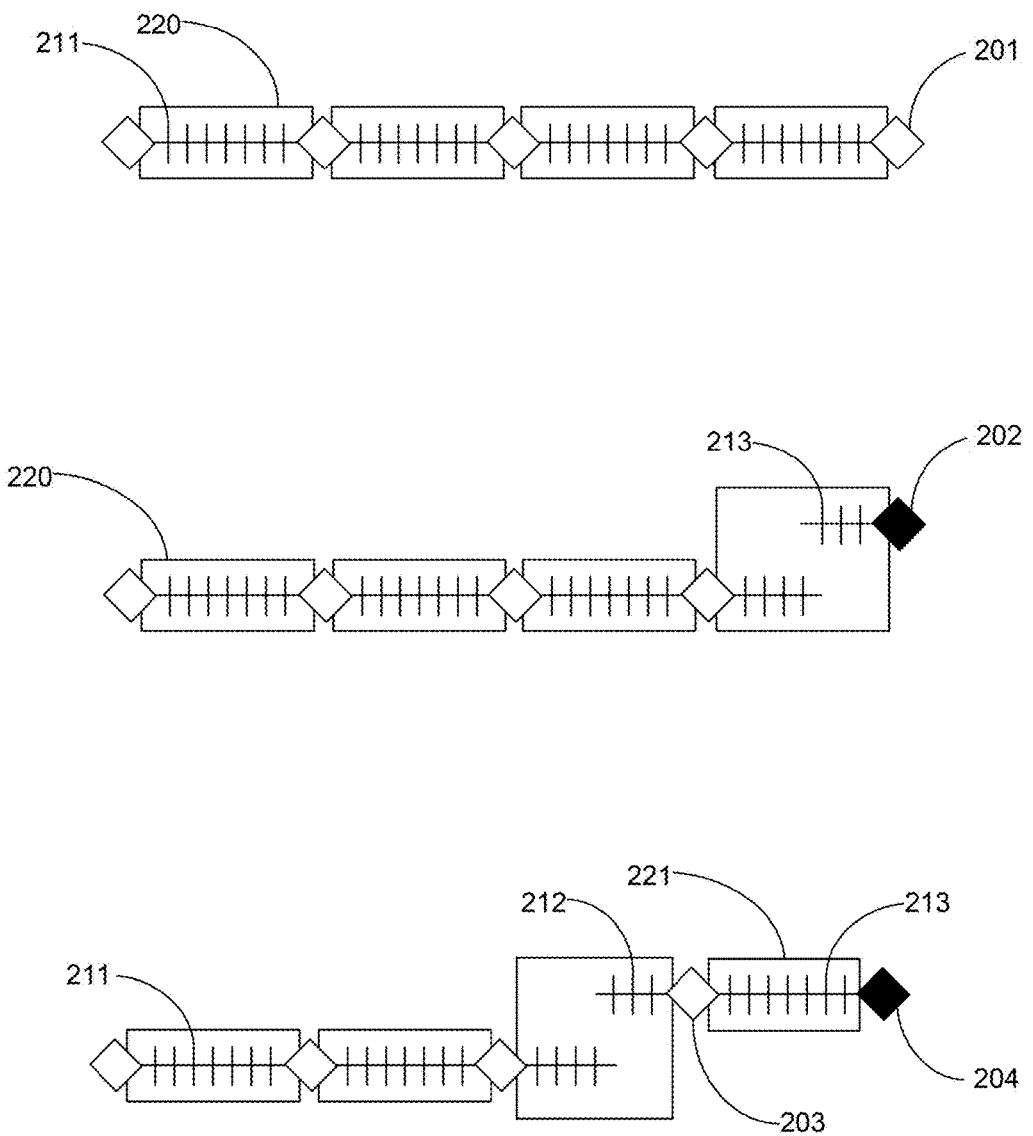
FIG. 2 illustrates three potential sequences of diagnostic test results.

FIG. 2 shows three potential sequences of test-results from diagnostic tests. The top row shows four sets of patient test results or QC intervals 220 where all the results are produced with no systematic error present. The time when each patient test result was obtained is indicated with a vertical line 211. A passed QC event 201 is shown as an open diamond before and after each QC interval. The second row shows four QC intervals where a test system failure occurred in the fourth QC interval. Affected results 213 are shifted relative to unaffected results. The failed QC event 202 following the test system error is shown as a black diamond. Since the affected results occurred after the last passed QC event they are correctible. The third row shows four sets of QC-intervals, where a test system failure occurred in the third QC-interval. The QC event 203 following the test system failure was passed. Final unreliable patient results 212 are among those affected results that occurred before the passed QC-event 203, whereas correctible unreliable patient results 213 are those that occurred after the last passed QC event 203 and before the first failed QC event 204.

It is in the interest of any operator of diagnostic equipment to limit both the number of correctible and final unreliable patient results. However, when there is a fixed amount of resources made available for quality control, the measures used to reduce the number of correctible unreliable patient results may adversely affect the number of final unreliable patient results and vice-versa. For example, if more reference samples are tested at each QC event, more patient specimens would be tested between each QC event to keep the effort expended on QC events about the same (e.g., ratio of QC events to patient specimens tested between QC events). While this shift may reduce the chance of final unreliable patient results, it may increase the expected number of correctible unreliable patient results after a QC failure. An approach for finding an appropriate balance is therefore needed.

B. Performance Targets

In an embodiment, good lab practice dictates that upon a QC failure, the operator will investigate the patient specimens that were tested between the previously passed QC event and the failed QC event. The incorrect patient results reported during this time may be referred to as correctible as the lab may retest these specimens and inform patients of the new, correct results. If incorrect results were reported prior to the last QC pass, these results may be referred to as final because the incorrect results will be the final report from the lab.

In another embodiment, practice is to retest a lower number of specimens. For example, if a lab tests 100 specimens between each QC event, it may decide to only retest the last 50 specimens following a QC event. In this case the incorrect results among those last 50 will be correctible, and any earlier incorrect patient results will be final.

In yet another embodiment, practice is to retest a greater number of specimens. A lab testing 100 specimens between each QC event may decide to retest the last 200 specimens on a QC failure. Similarly, any incorrect test result among the last 200 specimens will be correctible, and any incorrect test result prior to these will be final.

This window of retesting may be expressed as a factor of the number of specimens tested between each QC event. For example, if 200 specimens are tested and there are 100 specimens between each QC event, this factor would be 2. Where not otherwise stated, this factor of retesting will be assumed to be 1 as shown in FIG. 2.

When the factor of retesting is constant, the number of correctible unreliable patient results can be controlled by increasing or decreasing the number of patient specimens between QC events. For example, if a QC event is conducted between every 20 specimens, there will be no more than 20 correctible unreliable patient results following a QC failure.

In another embodiment this can be specified as an absolute maximum per test system failure. For example, it can be specified that in the event of a test system failure, there should be a maximum of 10 final unreliable patient results and 50 correctible unreliable patient results. In yet another embodiment this can be specified in terms of the expected number of unreliable patient results. For example, it may be specified that in the event of a test system failure, the expected number of final unreliable patient results should be no more than 5 and the expected number of correctible unreliable patient results should be no more than 10.

The QC utilization rate of a particular strategy may be expressed as the average number of reference samples tested at each QC event divided by the average number of patient specimens tested between QC events. For example if 100 patient specimens are tested between QC events and 6 reference samples are tested during each QC event then the QC utilization rate is 6/100=0.06=6%. This metric may be measured in a number of different ways.

In an embodiment a quality control strategy is selected such that it minimizes the QC utilization rate while meeting the performance targets.

In addition to the performance targets, the optimization may in an embodiment rely on certain properties of the diagnostic equipment, including a system stability factor ($P_F$) and a sigma metric ($\sigma_M$) of the system.

In one embodiment, the system stability factor ($P_F$) indicates the portion of system failures that result in a systematic shift at least as large as the quality specification for the analyte. For example, an unstable system may have a $P_F$=0.5, a moderately stable system $P_F$=0.25, and a stable system $P_F$=0.1. In this case, for the stable system, only 10% of system failures will result in a systematic shift as large or larger than the quality specification of the analyte.

In an embodiment, the sigma metric of the test system ($\sigma_M$) is used as a measure of the performance of the system. The sigma metric measures the ratio of the quality specification to the test system imprecision. For example, the sigma metric may be used to denote the portion of tested samples that have a measurement error less than the specified allowable total error ($TE_a$). In an embodiment where the test system imprecision is characterized by a standard deviation σ, the sigma metric is the ratio of the specified total allowable error to σ:

$$\sigma_M = \frac{TEa}{\sigma}.$$

This may in turn be used to determine the probability that samples are acceptable or unacceptable. See Westgard J O. Six Sigma Quality Design & Control. Madison, Wis.: Westgard QC, Inc., 2001.

III. Risk Acceptability Matrix

As previously stated, the risk of harm to a patient from incorrect measurements of an analyte depends on two factors: the severity of harm and the probability of occurrence of the harm. The analysis presented in the previous section only accounts for the probability of occurrence of the correctable and final unreliable patient results. The severity of harm can be taken into consideration when analyzing a QC strategy. Various standards organizations have established correlations between severity of harm and acceptable probability of harm, as now explained.

A. Severity of Harm

FIG. 3 shows a risk acceptability matrix 300 according to embodiments. The risk acceptability matrix 300 relates categories for the severity of harm (top row) to corresponding qualitative levels of acceptable probability of the harm (left column). The severity of harm is classified into five categories, from negligible to catastrophic. For example, in some cases, negligible harm could be defined as having only mild discomfort for the patient, with no other side effects. At the other extreme, catastrophic harm could be defined as harm causing extreme pain, long-term disability or death.

For a given severity of harm, the risk acceptability matrix indicates whether a corresponding probability of harm is acceptable or unacceptable. For example, if the severity of harm that would result from acting on an incorrect measurement was serious, such as not administering an antibiotic, the probability of such an incorrect measurement would only be acceptable if it were only occasional, remote or improbable. Alternatively, if the severity of harm is judged to be catastrophic, then only the least probable level of occurrence could be accepted. Other risk acceptability matrices may use a different number of categories for the severity of harm, or different levels for the acceptable probability of harm.

Such categories and definitions often rely on a common understanding of the word choices and examples used. Severity of harm may be difficult to quantify, and can depend on factors specific to a patient (such as age or pre-existing chronic conditions). In some embodiments, severity of harm can be an input used to determine the acceptability of a QC process. The acceptable level of probability of harm can be assigned quantifiable levels, as now discussed.

B. Acceptable Probability of Harm

The probability of harm categories of FIG. 3 can serve as a basis for quantifiable standards for use in analyzing a QC strategy. Such standards can be based either on probability of occurrence or on frequency of occurrence.

FIG. 4 is an exemplary table 400 that relates the qualitative probability of harm categories (left column) for an incorrect test result to corresponding frequencies of occurrence (middle column) or numerical probability values (right column). The category levels for the qualitative probability of harm in the left column of FIG. 4 correspond to the probability of harm categories in the left column of FIG. 3. The middle column is a standard based on frequency of occurrence of the incorrect test result developed by the Clinical Laboratories Standards Institute (CLSI). The right column is a standard developed by the International Organization for Standardization (ISO). Various embodiments may make use of other standards, or revisions/updates to these standards.

In table 400 in FIG. 4, "occasional" probability of harm is defined to be either one that has a frequency of occurrence of once per year (by the CLSI standard) or as one with probability value less than $10^{-4}$ but greater than or equal to $10^{-5}$ (the ISO standard). A user analyzing a QC strategy may find either of these standards more useful, based on how reliability parameters of the measurement equipment are expressed by the manufacturer or by parameters of the QC strategy. For example, if the measurement equipment is used at a steady rate of tests per time period then the CLSI standard may be more easily used, whereas alternatively if the test equipment's validation data specifies the probability of error of a test numerically, the ISO standard might be preferred. Note that knowing the number of tests performed per time period can allow a user to convert between the two standards.

In various embodiments, design of a QC strategy may make use of the risk acceptability matrix of FIG. 3 and the table of FIG. 4 in conjunction. For example, if the potential harm to a patient caused by hazardous medical action based on an incorrect test results are judged to be serious, then by FIG. 3 the QC strategy should ensure such incorrect test results occur only with a frequency that is "Occasional." FIG. 4 would then give that such incorrect test results occur once a year, or with an acceptable probability between $10^{-5}$ and $10^{-4}$.

IV. Determination of Predicted Probability of Harm

The description in the previous section showed how to determine an acceptable probability of harm according to a risk acceptability matrix and established standards, once given a severity of patient harm. What is needed next is a way to calculate the probability of harm using known parameters of the test equipment, the details of the QC strategy of a testing process for the particular instrument measuring the particular analyte, and how the test results are used in patient care. Such a prediction can be compared to the acceptable probability of harm to determine if the QC strategy is appropriate.

Embodiments for analyzing a QC strategy can calculate the probability of harm $P_H$ from parameters of the QC strategy by means of the formula:

$$P_H = \{P_E(0) + E(N_{uf})/MPBF\} \cdot P_{h|u} \quad (1)$$

Each of the terms occurring in this formula will now be explained. In formula (1), the first term within the brackets, $P_E(0)$, is the probability the test system reports an incorrect result while operating correctly, i.e. in an in-control state. The second term within the brackets, $E(N_{uf})/MPBF$, is the ratio of the expected number of incorrect final patient results to the mean number of specimens examined between test system failures, and so gives the proportion of patient results that are incorrect due to test system failure. The bracket term is then the combined probability of incorrect results during in-control and out-of-control (test system failure) states. Thus multiplying by the conditional probability of harm given an incorrect result, $P_{h|u}$, yields the calculated probability of harm. Each of these terms will now be explained in further detail.

A. Inherent Probability of Error: $P_E(0)$

The term $P_E(0)$ is the probability that the test system reports an incorrect result when it is in control and operating as expected. While ideally it would be zero, no instrument is perfect, and the test system's measurements are subject to random variation about the true values of the quantity under test. In typical test systems with quality instruments $P_E(0)$ is very small. $P_E(0)$ is determined by the test system's bias and imprecision, and additionally the allowable total error requirements for the analyte. As an example of the second requirement, allowing an error of ±5% in a blood glucose measurement from an instrument with a coefficient of variation of 2.5% produces a higher $P_E(0)$ than allowing an error of ±10%.

B. Expected Number of Unreliable Final Errors: $E(N_{uf})$

The value $E(N_{uf})$ is the expected number of incorrect final results reported due to a test system failure. It can be determined based on parameters of the QC strategy in use. For example, if QC events are performed after every 100 patient tests, $E(N_{uf})$ can be expected to be higher than if QC events are performed after every 50 patient tests. Further details on the calculation of $E(N_{uf})$ are provided in subsection E below.

C. Mean Number of Patient Results Between Failures: MPBF

MPBF is the mean number of patient results reported between test system failures, i.e., the average number of individual tests performed before the test system fails to operate as expected. It measures the reliability of the test system. Typically, it is a value provided by the laboratory or operator of the test system, and is based on experience with the test instrument.

D. Probability an Incorrect Result Leads to Patient Harm: $P_{h|u}$

The last term $P_{h|u}$ is the conditional probability that an incorrect patient result reported by the test system will lead to an inappropriate action that causes patient harm. It depends on how influential the test result value for the analyte is in the medical decision making process. It is often based on medical judgment and experience on how the test result value is used in patient treatment. This probability assessment is not intended to reflect the severity of the harm associated with an inappropriate action, only the likelihood of an inappropriate action.

Formula (1) provides a way to account for the separate influences that can contribute to the probability of patient harm. It distinguishes those factors that depend on medical judgment or knowledge of the testing equipment, from the factor $E(N_{uf})$ that is determined based on the QC strategy. How $E(N_{uf})$ is determined from the parameters of the QC strategy is now explained.

E. Details of the Calculation of $E(N_{uf})$

Figure 5:
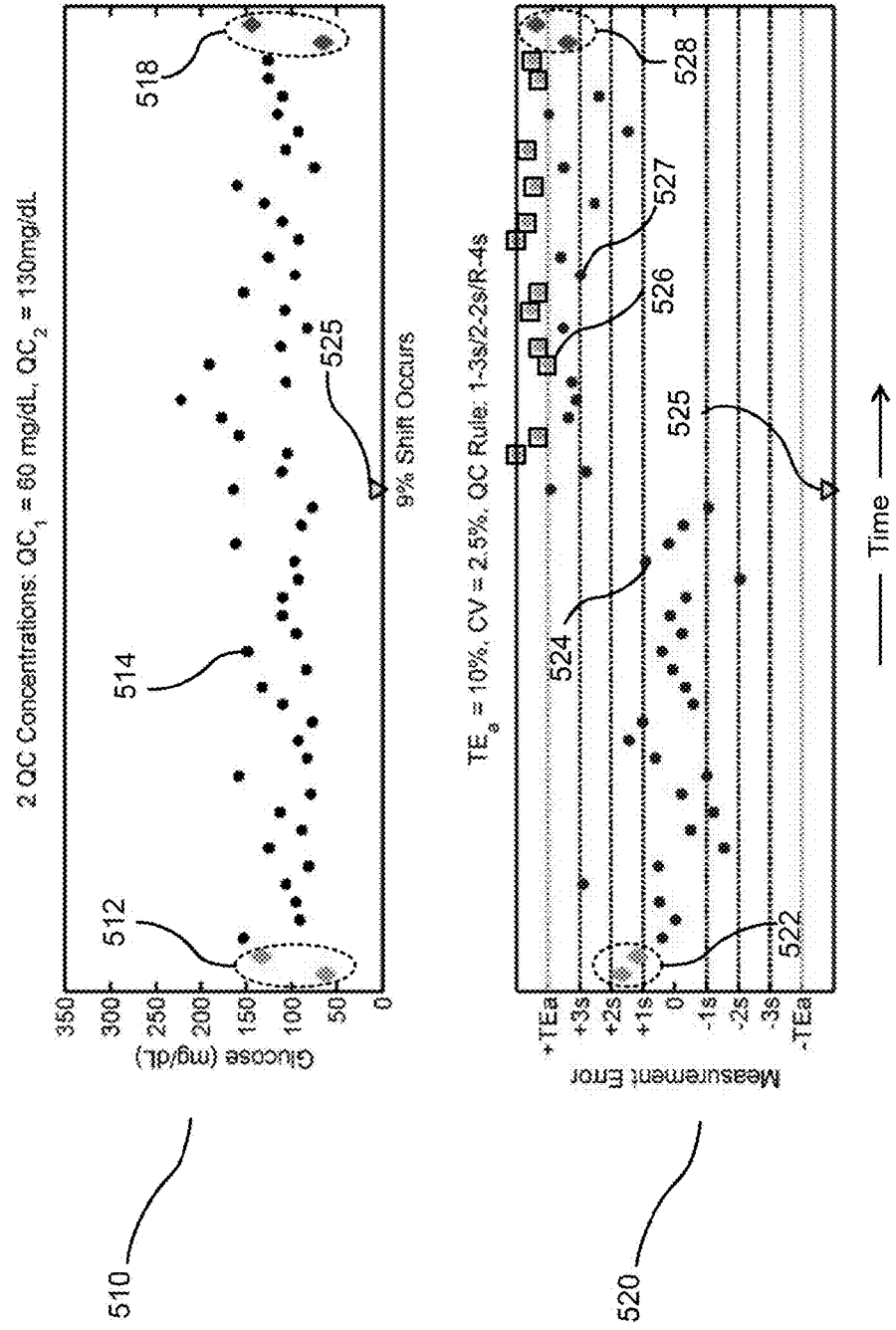
FIG. 5 illustrates an example of a time-correlated sequence of instrument measurements.
Figure 6:
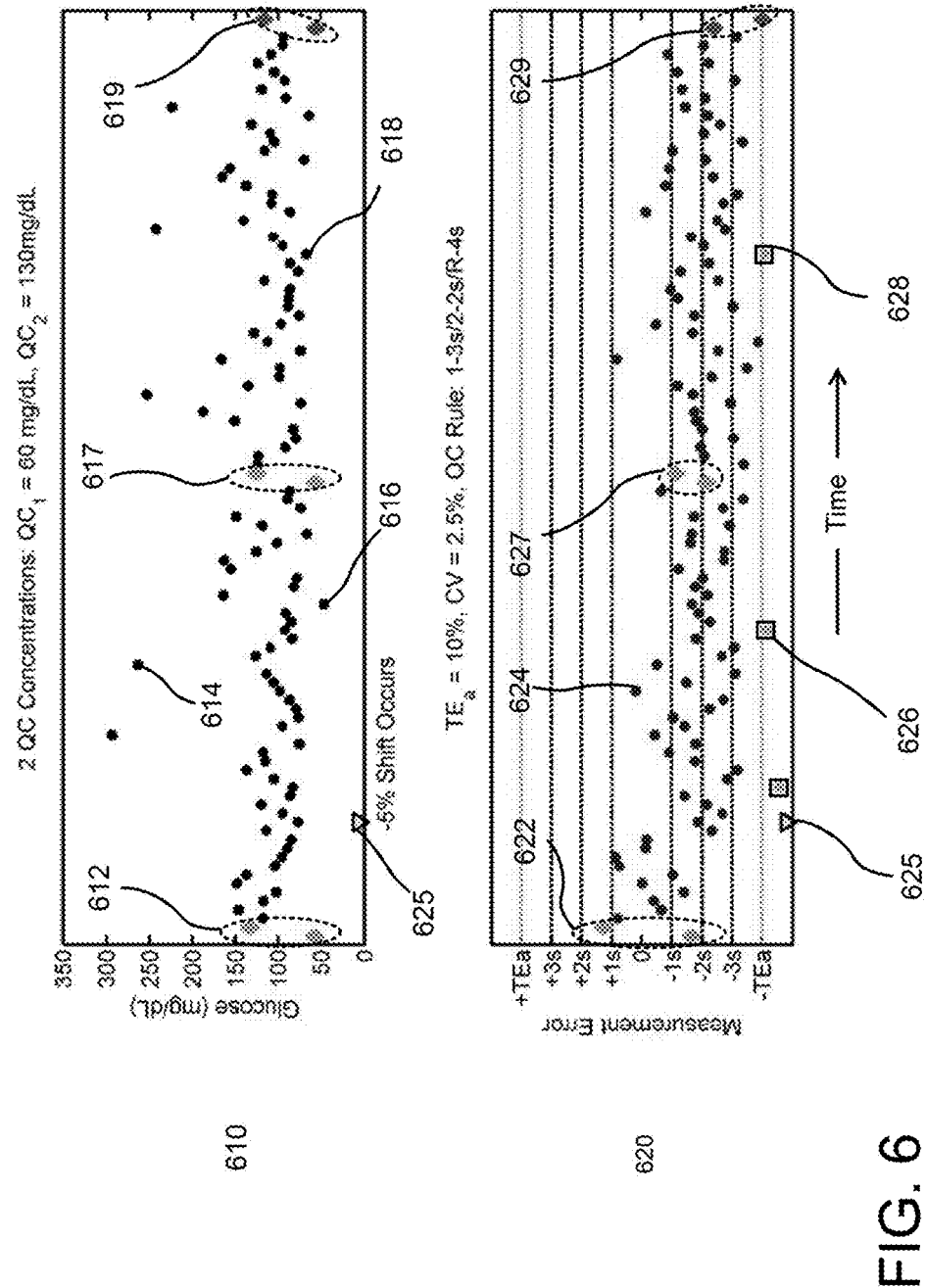
FIG. 6 illustrates an example of a time-correlated sequence of instrument measurements.

FIG. 5 and FIG. 6 show two examples of simulated sequences of test results to explain the details for the calculation of $E(N_{uf})$. These are more detailed cases of the example sequences described in FIG. 2. In FIG. 5 the top graph 510 shows observed patient results for blood glucose measurements. An initial QC event 512 measures two QC reference samples, shown as diamonds, the first sample at 60 mg/dl and the second at 130 mg/dl. The second graph 520 shows the measurement errors in the test results; only the QC reference sample measurement errors would be known by test system operators, whereas the patient result measurement errors are included to explain the various concepts discussed here. At the first QC event 512 the instrument is determined to be operating correctly according to the QC strategy since the errors in the reference sample measurements 522 meet the QC strategy's decision rule of $1_{3s}/2_{2s}/R_{4s}$, for a coefficient of variation (CV) of 2.5% and a $TE_a$ of 10%.

The instrument is then used in practice to obtain a sequence of 50 patient results 514 until the next QC event test 518 is performed. Even during in-control operation the patient results may have measurement errors 524 with respect to their true values, as shown in 520. At time instant 525 the test instrument or system suffers a failure that causes the subsequent patient results to undergo a 9% shift in measured values. This may not be readily apparent to test system operators based on the observable test result values in 510. After time 525, some of the subsequent patient results 526 may have measurement errors that exceed what is deemed medically tolerable and so have potential to lead to patient harm, while other subsequent patient results 527 may have measurement errors that are still within tolerable limits.

At the end of the QC interval a QC event determines that measured control values 518 have errors 528 that fail the QC strategy. As the time 525 at which the test system failure occurred cannot be known to operators, the operators can only conclude that any of the previous 50 patient results could be incorrect. If the patient specimens can be retested, the incorrect results are correctible.

FIG. 6 shows alternate simulated data for the same blood glucose measurement system and QC strategy described for FIG. 5. Initial control test results 612 show that the system is in an in-control state since the observable errors 622 meet the QC strategy criteria. At time 625 a test system failure causes the measured values to undergo a −5% shift. At a second QC event, measured control test values 617 have errors 627 that lead system users to conclude incorrectly that the test system is still in an in-control state. This corresponds to the third row of FIG. 2. Because the shift in the test results due to the test system failure is relatively small, for many patient results 614 the difference 624 from their true values is still within acceptable limits. However, for patient result 616 the actual measurement error 626 is outside of acceptable limits. Similarly, for most patient results after the second QC event, despite the instrument change, most patient result measurements have errors that are within acceptable limits of the true value. But there can still be a patient result 618 whose measurement error 628 is outside the limits.

At the third QC event the control test results have observable errors 629 that indicate a failure of the test system. Consequently, the patient results that follow the second QC event are correctible, whereas the patient results between the initial and second QC events—if reported out according to the QC strategy—would be final.

The two simulated examples of FIG. 5 and FIG. 6 illustrate a number of factors that can influence the value of $E(N_{uc})$, the number of correctible unreliable patient results, and $E(N_{uf})$, the number of final unreliable patient results.

These factors include how many QC intervals prior to a failed QC event are treated as unreliable and retested. The simplest strategy is to treat all the test results of only the QC interval immediately preceding the failed QC event as unreliable and retested. Stronger strategies may treat as unreliable the test results of a higher number of preceding QC intervals. Weaker strategies, which might be used if the probability of harm category from FIG. 3 is Negligible, would only retest a fraction of the test results from the preceding QC interval. Other factors that can influence $E(N_{uf})$ include the QC rule, the value of $TE_a$, and the number of patient results in the QC interval.

Another important factor influencing $E(N_{uf})$ is the size of the shift that occurs because of a test system failure. Note from FIG. 5 how the larger shift of 9% leads to a greater number of patient results 526 that exceed the $TE_a$ limit, but that the following QC event is more likely to detect that a test system failure has occurred. Thus, assuming the simplest strategy stated above, the value of $E(N_{uc})$ will be higher but $E(N_{uf})$ will be lower. In contrast, FIG. 6 shows that for a smaller test system failure shift of −5% there are fewer overall incorrect patient results. However, using the same QC strategy, the incorrect patient results 626 are reported as final, leading to a higher value of $E(N_{uf})$ and a reduced value of $E(N_{uc})$.

Figure 7:
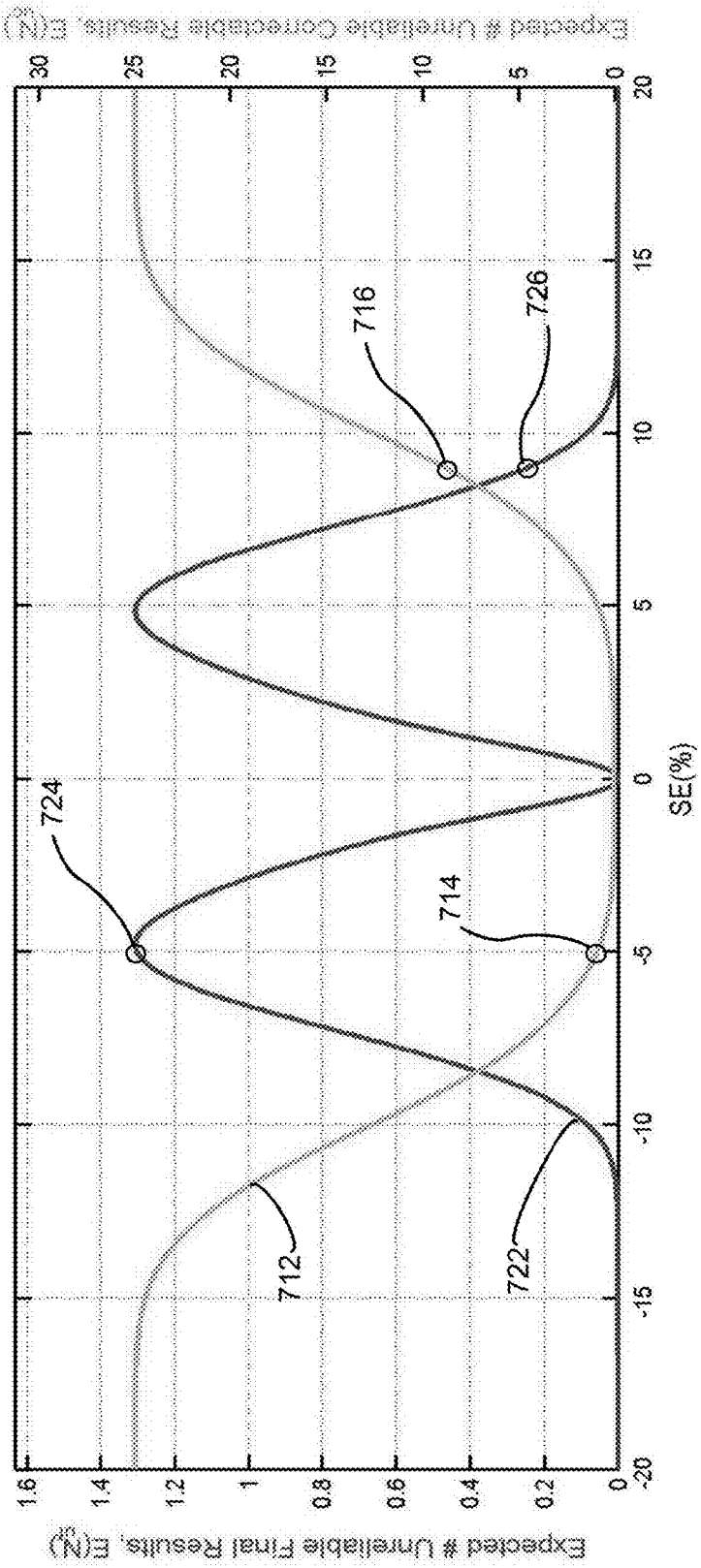
FIG. 7 illustrates graphs of expected numbers of unreliable results, according to an embodiment.

FIG. 7 shows the values of $E(N_{uc})$ and $E(N_{uf})$ (respective plots 712 and 722) under the simulation conditions used for FIGS. 5 and 6, plotted as functions of the size of the test system failure, which is expressed as a systematic error (SE). Both are zero for SE=0. For small values of SE, situations as in FIG. 6 predominate, leading to larger $E(N_{uf})$ and relatively smaller $E(N_{uc})$ as shown by the data points 714 and 724 for the simulation of FIG. 6. But for larger values of SE, it becomes less likely that a QC event will fail to detect the test system failure, so the incorrect patient results are more likely to be correctible rather than final results. This is shown by the data points 716 and 726. The functions for $E(N_{uc})$ and $E(N_{uf})$ can be determined based on the parameters of the QC strategy. Methods for determining analytic formulas for $E(N_{uc})$ and $E(N_{uf})$ are explained in detail in U.S. Pat. No. 8,738,548.

Because it is possible for the size of the shift SE caused by test system failure to vary, to determine the overall value of $E(N_{uf})$ for the QC strategy, it is necessary to assign a probability distribution to the range of possible values of SE and integrate $E(N_{uf})$ in terms of SE with respect to that probability distribution. In may be the case that the size of the test system failures are known by the system operators to lie within a certain interval. For the situation of FIGS. 5 and 6 the blood glucose measurement equipment has test system failures producing shifts between −20% and 20%, with any value being equally likely. In this situation the probability distribution is taken to be a uniform distribution. In other applications and embodiments, for other test equipment, other probability distributions such as Gaussian, Poisson or others known in the art, may be appropriate.

Figure 8:
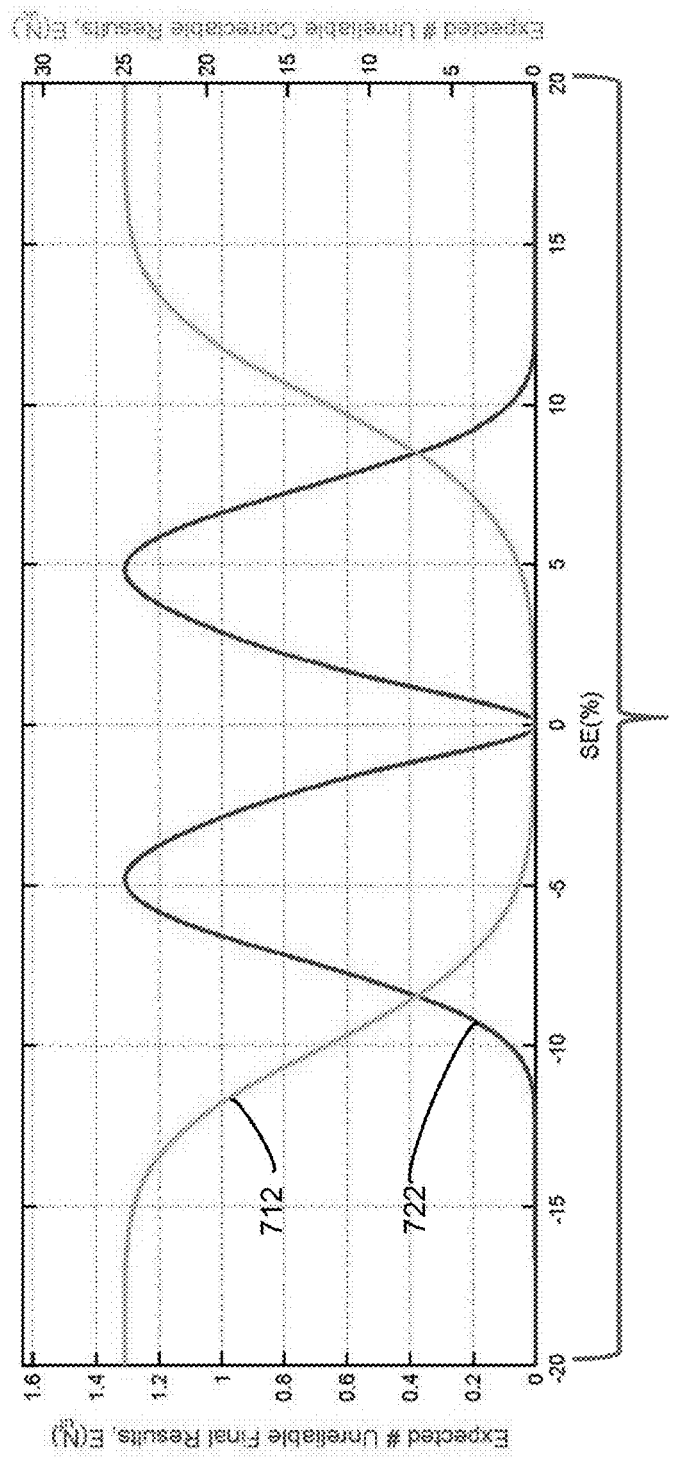
FIG. 8 shows graphs of expected number of unreliable results as used to determine an expected number of unreliable final results, according to an embodiment.

FIG. 8 illustrates the calculation of the overall value of $E(N_{uf})$ for the QC strategy of the situation of FIGS. 5 and 6:

$$\text{Overall } E(N_{uf}) = \frac{1}{0.4} \int_{-0.2}^{0.2} E(N_{uf})(SE) \, dSE$$

Without using the explicit analytic form for the function $E(N_{uf})(SE)$, the value above can be obtained by approximating the curve 722 as two triangles, so that:

Overall $E(N_{uf}) \approx 2*(\frac{1}{2})*(1.3)*(0.10)/0.4 = 0.33$

In some embodiments the function $E(N_{uf})(SE)$ may only be known numerically at various sample points, rather than from an analytic expression. In such embodiments the integral for the overall value of $E(N_{uf})$ can still be computed by appropriate known numerical techniques, for example, Simpson's Rule, Gaussian quadrature, or Clenshaw-Curtis quadrature. Such numerical methods may also be used for cases when function $E(N_{uf})(SE)$ is given by an analytic expression.

V. Determination Whether QC Strategy is Acceptable

The various quantities just explained are now used with formula (1) as part of a method to determine if a QC strategy is acceptable. An acceptable QC strategy is one whose user-selectable parameters, such as number of patient tests performed in a QC-interval, lead to a predicted probability of harm that is better (less than or equal to) the acceptable probability of harm.

A. Analysis Method

Figure 9:
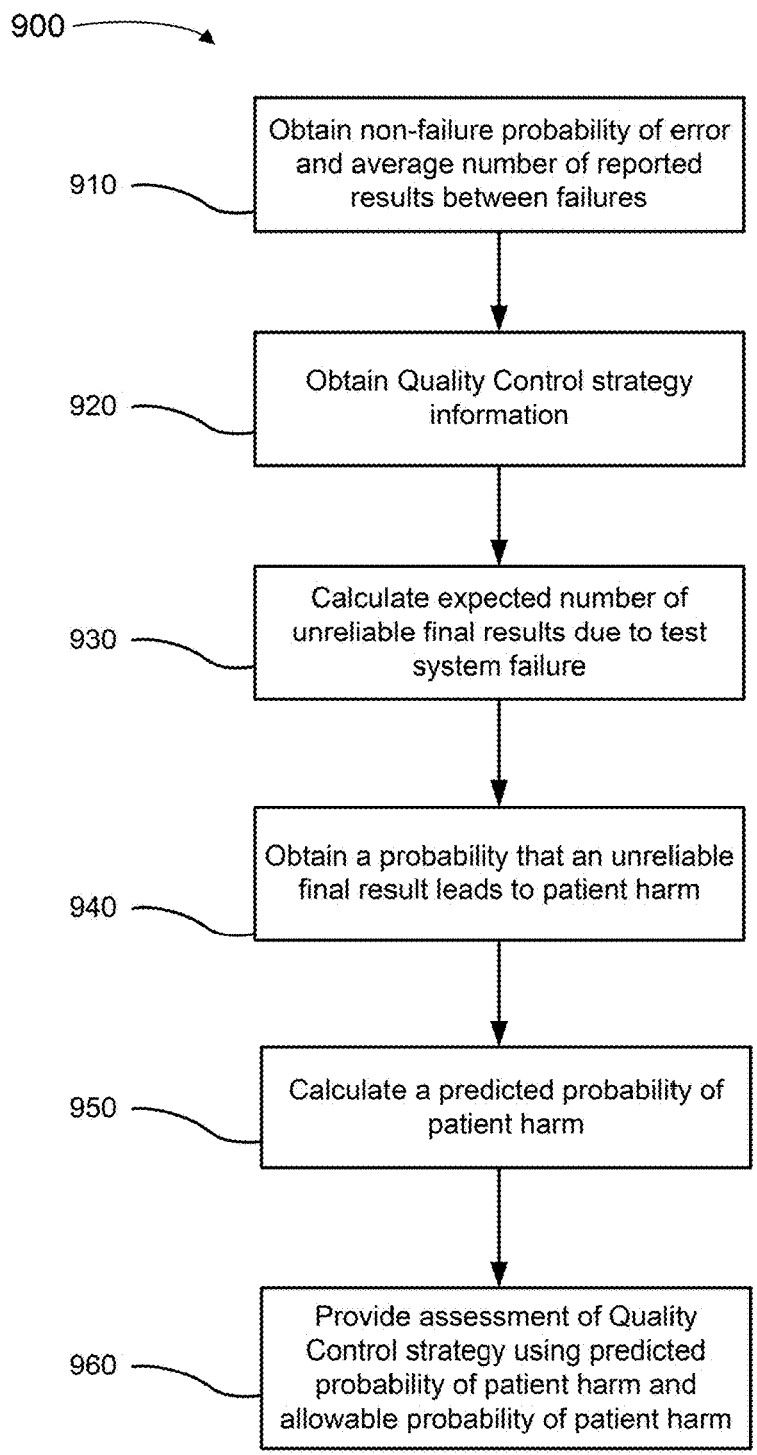
FIG. 9 is a flow chart of a method of assessing a Quality Control strategy, according to an embodiment.

FIG. 9 shows a flow chart of a method 900 for analyzing a QC strategy adopted for a testing process for an analyte that uses a particular instrument. In some embodiments the analysis is performed on a computer system, such as described below in relation to FIG. 11 and FIG. 12.

At stage 910, a computer system obtains a probability $P_E(0)$ of reporting incorrect patient results while the test system has not had a failure. As discussed above, $P_E(0)$ is typically very small and may be determined by the test system's bias and imprecision and the allowable total error requirements for the analyte. The mean (i.e., average) number of patient results reported between failures (MPBF) of the particular instrument may be determined by manufacturer's specifications and/or user experience.

At stage 920, information about the QC strategy is obtained. The information can include values of parameters such as the number of patient tests performed between QC events, the QC decision rule, and how many patient specimens are retested after a failed QC event is detected. Other QC strategies may use other parameters, which may be obtained by the computer system as needed for calculation of the values discussed below.

At stage 930, the expected number of unreliable final results $E(N_{uf})$ due to a failure of the test system is calculated. The calculation may use the QC strategy information and/or other information about the test equipment. The calculation can use methods such as those explained above in Section IV.E.

At stage 940, a probability $P_{h|u}$ that an incorrect result leads to patient harm is obtained. $P_{h|u}$ does not necessarily reflect the severity of the harm associated with an inappropriate action, only the likelihood of patient harm.

At stage 950, a predicted probability of harm $P_H$ is calculated using formula (1) and the values of $P_E(0)$, MPBF, $E(N_{uf})$, and $P_{h|u}$. This can be performed in a computer system by first computing a proportion of patient results that are incorrect due to a failure of the particular instrument, the proportion including $E(N_{uf})$ divided by MPBF. The computer system then can compute a combined probability of incorrect results by adding $P_E(0)$ and that proportion. Next, the computer system can calculate $P_H$ as the product of the combined probability of incorrect results with $P_{h|u}$.

At stage 960, the QC strategy is assessed by comparing the calculated $P_H$ to an acceptable probability of harm. The acceptable probability of harm can be determined by using a severity of harm resulting from an inappropriate action based on an incorrect test result and a risk acceptability matrix. The resulting assessment of the QC strategy is then output to a user, who can either implement or modify QC strategy based on the assessment.

The assessment of stage 960 can be by comparison of the calculated $P_H$ to the acceptable probability of harm, such as whether Predicted $P_H \le$ Acceptable $P_H$. The acceptable probability of harm can be determined from a risk acceptability matrix as in FIG. 3 and probability of harm table, as in FIG. 4. Other methods of assessing of the QC strategy may be used, as now described.

B. Calculation of $RMI_P$

It may be desirable to adopt a standardized, more direct way to assess a QC strategy than judgments based directly on the value of the predicted $P_H$. The value of the predicted $P_H$ may vary with the analyte and instrument, so that the numerical value of the predicted $P_H$ may not provide immediate assessment of the QC strategy, the value of the acceptable $P_H$ also matters. As now explained, in some embodiments a standard way to assess a QC strategy uses the proportion of the predicted $P_H$ to the acceptable $P_H$.

One standardized method for assessing of a QC strategy includes forming a patient Risk Management Index ($RMI_P$) and applying decision criteria on the value of the $RMI_P$. The $RMI_P$ is defined as:

$$RMI_P = \frac{\text{Predicted } P_H}{\text{Acceptable } P_H}.$$

If it is the case that $RMI_P \le 1$, then the risk is considered acceptable, and the QC strategy is assessed as meeting the criteria embodied in the risk assessment matrix. There are various advantages to using $RMI_P$. As a ratio, it can express how well a QC strategy meets an acceptable risk criteria ($RMI_P$ well below 1). This can permit revision of the QC strategy for either cost savings or reduced risk of harm. It allows easy assessment and comparison of QC strategies for multiple analytes, with different frequencies of test system failure, different probabilities of harm given an incorrect result and different severities of patient harm. It provides a standard figure of merit for evaluating a QC strategy. It can be implemented in a computer system so that the values obtained in the method of FIG. 9 are the user inputs, allowing for rapid calculation.

C. Example Assessment of a QC Strategy

An illustrative example for analyzing a QC strategy is now presented. In this example, the mean number of days between test system failures is 120 days. The average number of patient results produced each day is 50. Thus MPBF=120*50=6000. The conditional probability of harm from an incorrect reported patient result, $P_{h|u}$, is 0.5, reflecting that the analyte provides important and sensitive information. The severity of harm is considered Serious. From FIG. 3, the acceptable frequency of harm is "Occasional." According to the EP23 standard of FIG. 4, Occasional corresponds to 1/year. Thus the Acceptable $P_H$ equals 1/(60*365)=1/18,250.

The allowable total error requirement $TE_a$ is 10%. The testing method has a CV=2.4%, and a Bias=0. This allows the value of $P_E(0)$ to be computed as 1/32,354. The QC strategy uses 2 control concentrations at each QC event, uses the rule $1_{3s}/2_{2s}/R_{4s}$, with QC events once per day (every 50 analyte examinations), similar to the example presented in FIG. 5. As explained in relation to FIG. 8, assuming an equiprobable distribution for the size of the errors, $E(N_{uf})$ is found by integration of the red curve and yields the value of 0.33 for this QC strategy.

With these values, using formula (1) yields that the Predicted $P_H$ for this QC strategy is 1/23,281. The Allowable $P_H$ is 1/18,250. Thus $RMI_P=(1/23,281)/(1/18,250)=0.78$. As $RMI_P<1$, therefore patient risk is deemed acceptable.

VI. Determination of Optimal QC Strategy

The previous sections disclose methods and systems for analyzing a given QC strategy from the information of the test system and the parameters of the QC strategy. But in order to determine a QC strategy that meets an acceptable probability of harm, embodiments can work backwards to the parameters of the QC strategy.

A. Determination of Allowable $E(N_{uf})$

Of the quantities in formula (1), $P_E(0)$ is based on how much error in the measurement of the analyte can be tolerated and the test method's measurement imprecision when operating correctly. The value of MPBF is determined from the reliability of the test method. Next, clinical experience and judgment can be used to establish $P_{h|u}$, based on how the test values for the analyte are used. Thus, user-selectable parameters of the QC strategy only influence the value of $E(N_{uf})$. Examples of such parameters of the QC strategy include number of patient samples tested between QC events, the number of reference samples tested at a QC event, and the QC strategy's decision rule.

B. Determination of QC Strategy from Allowable $E(N_{uf})$

By inverting formula (1), it is possible to determine a formula for a maximum allowable $E(N_{uf})$ using obtained values of $P_E(0)$, MPBF, $P_{h|u}$, and severity of harm. Values for the various user-selectable parameters of a QC strategy can then be selected in order that the $E(N_{uf})$ of the resulting QC strategy is no more than the maximum allowable $E(N_{uf})$. An acceptable QC strategy satisfies Predicted $P_H \leq$ Max Acceptable $P_H$. The value on the right is denoted $MaxP_H$, and can be used as an upper limit for formula (1):

$$\{P_E(0)+E(N_{uf})/MPBF\} \cdot P_{h|u} \leq MaxP_H$$

When this is inverted, the result becomes:

$$E(N_{uf}) \leq MPBF^*\{MaxP_H/P_{h|u}-P_E(0)\} \quad (2)$$

This value on the right is denoted $E(N_{uf})_{ALLOWABLE}$.

Parameters of the QC strategy can now be used to calculate a corresponding value for $E(N_{uf})$. When it is less than $E(N_{uf})_{ALLOWABLE}$, the QC strategy can be considered acceptable. If not, the parameters of the QC strategy can be modified.

As an example, consider the values discussed above in Section IV. C. The MPBF is determined to be 7200, $P_E(0)=1/32354$, the conditional probability of harm from an incorrect patient result is 0.5, and the severity of harm is considered Serious. By the criteria of FIG. 4, Max $P_H=1/(50*365)$. Using formula (2) one obtains $E(N_{uf})_{ALLOWABLE}=0.472$. If a laboratory's QC strategy produces an $E(N_{uf})$ with value less than or equal to 0.472, then the laboratory's $RMI_P$ is less than or equal to 1, and patient risk is acceptable. But if a laboratory's QC strategy produces an $E(N_{uf})$ greater than 0.472, the lab's $RMI_P$ is greater than 1, and patient risk is unacceptable.

The example just presented also exemplifies a method that can be used to select parameters to ensure that a QC strategy is adequate, i.e. is such that the probability of patient harm is within acceptable limits. The method comprises determining a maximum allowable expected number of unreliable final patient results, $E(N_{uf})_{ALLOWABLE}$, and adjusting the parameters the QC strategy that can be controlled so that the $E(N_{uf})$ of the resulting QC strategy is no more than $E(N_{uf})_{ALLOWABLE}$.

Figure 10:
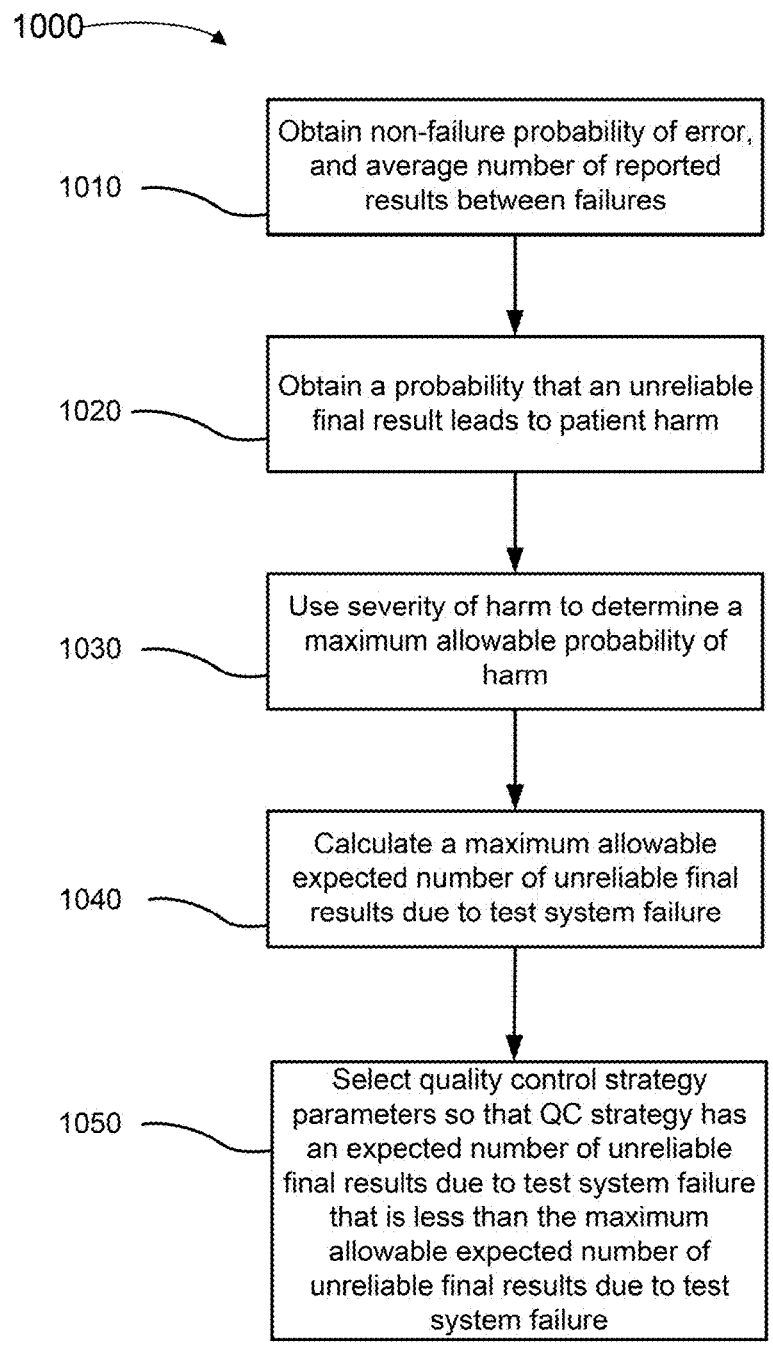
FIG. 10 is a flow chart of a method of selecting parameters for a Quality Control strategy, according to an embodiment.

FIG. 10 illustrates a flow chart for such a method. In some embodiments the computations involved are performed on a computer system, such as described below in relation to FIG. 11 and FIG. 12.

At stage 1010, a computer system obtains a probability $P_E(0)$ of reporting incorrect results while the test system has not had a failure, and a mean number of patient results reported between failures (MPBF) of the particular instrument. As discussed previously, these values depend on the instrument and not on the parameters of the QC strategy.

At stage 1020 the computer system obtains the conditional probability that an unreliable final result of the test system leads to patient harm, $P_{h|u}$. As stated previously, $P_{h|u}$ does not necessarily reflect the severity of the harm associated with an inappropriate action, only the likelihood of an inappropriate action.

At stage 1030, the severity of harm that can result from an unreliable final result is used to determine a maximum acceptable probability of harm, $MaxP_H$. This can be determined by using a risk acceptability matrix and a corresponding table of probabilities. For example, if the severity of harm is critical, from the risk acceptability matrix of FIG. 3 the probability of harm is required to be Remote. From table of FIG. 4, the numerical probability from the ISO standard for a Remote probability of harm is required to be less than $10^{-5}$. That is, $MaxP_H=10^{-5}$.

At stage 1040, a maximum allowable expected number of unreliable final patient results due to test system failure, $E(N_{uf})_{ALLOWABLE}$ can be calculated using the value of $MaxP_H$ determined in 1030, the values of $P_E(0)$ and MPBF obtained in 1010 and the value of $P_{h|u}$ obtained in 1020. From formula (2), the ratio $MaxP_H/P_{h|u}$ expresses a probability of an unreliable final patient result. By subtracting the contribution to this probability of incorrect results from when the test system is in control, $P_E(0)$, one obtains the probability of incorrect final results due to undetected test system failure. Multiplying this by MPBF yields the expected number of incorrect final results due to undetected test system failure. This is a quantity that the QC strategy seeks to control.

Then at stage 1050, the values of the parameters of the QC system can be selected so that, with those selected parameters, the QC has a calculated value of $E(N_{uf})$ that is less than $E(N_{uf})_{ALLOWABLE}$. Examples of the parameters of the QC system include the interval between QC events that monitor the particular instrument and the number of reference samples tested at each QC event.

The embodiments disclosed above can be partially automated by implementation on a computer system. Such automation allows users to analyze a QC strategy by input the QC strategy's parameters along with the values of $P_E(0)$, MPBF, the severity of harm and $P_{h|u}$ to determine the value of $E(N_{uf})$ for the QC strategy. The risk acceptability matrix and the probability of harm table can also be preprogrammed in the computer system, and may be updatable as the standards behind them change. An example of a computer system that maybe used to enable various embodiments is now disclosed.

VII. Computer System

Figure 11:
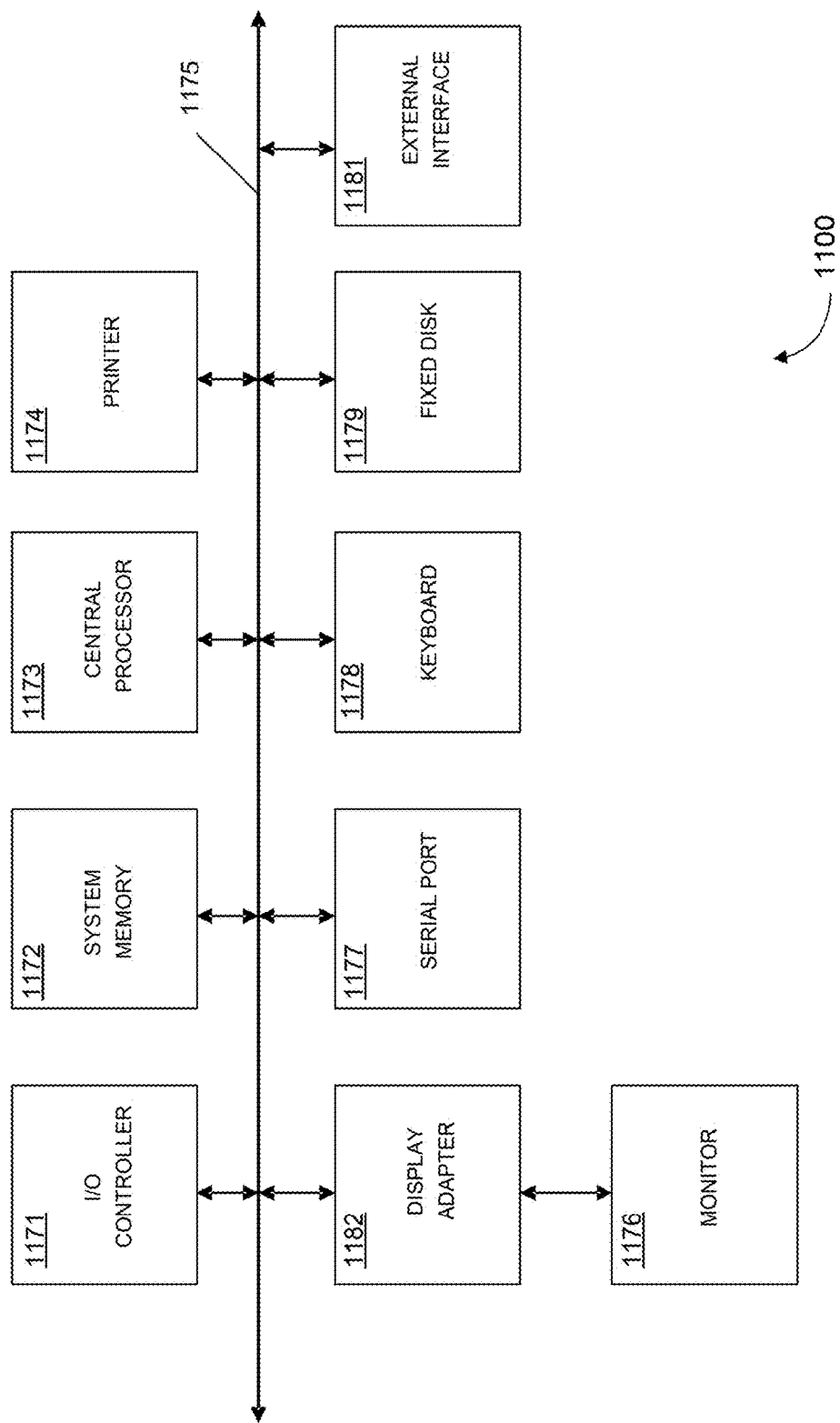
FIG. 11 shows a block diagram of an example computer system usable with system and methods according to embodiments of the present invention.

The subsystems shown in FIG. 11 are interconnected via a system bus 1175. Additional subsystems such as a printer 1174, keyboard 1178, fixed disk 1179, monitor 1176, which is coupled to display adapter 1182, and others are shown. Peripherals and input/output (I/O) devices, which couple to I/O controller 1171, can be connected to the computer system by any number of means known in the art, such as serial port 1177. For example, serial port 1177 or external interface 1181 can be used to connect computer system 1100 to a wide area network such as the Internet, a mouse input device, or a scanner. The interconnection via system bus 1175 allows the central processor 1173 to communicate with each subsystem and to control the execution of instructions from system memory 1172 or the fixed disk 1179, as well as the exchange of information between subsystems. The system memory 1172 and/or the fixed disk 1179 may embody a computer readable medium. Any of the values mentioned herein can be output from one component to another component and can be output to the user.

A computer system can include a plurality of the same components or subsystems, e.g., connected together by external interface 1181. In some embodiments, computer systems, subsystem, or apparatuses can communicate over a network. In such instances, one computer can be considered a client and another computer a server. A client and a server can each include multiple systems, subsystems, or components, mentioned herein.

Figure 12:
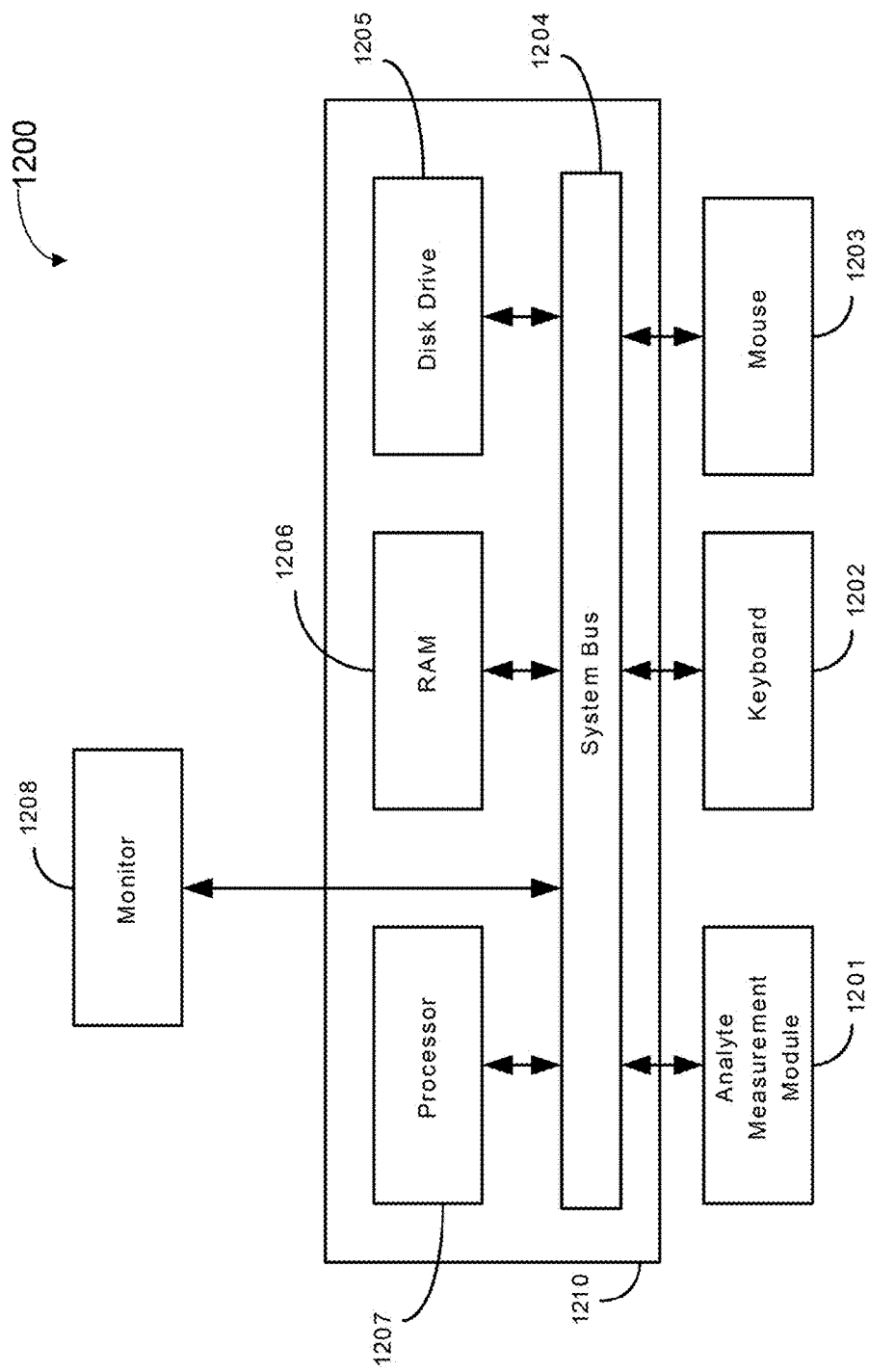
FIG. 12 is a block diagram of an apparatus for determining one or more properties of a biological sample according to embodiments of the present invention.

FIG. 12 is a block diagram of an apparatus 1200 that can be used to execute any of the embodiments. Apparatus 1200 includes a computer system 1210 and has a number of input modules. An analyte measurement module 1201 is used to measure the analyte responses in a test sample. This module can vary between different embodiments depending on the measurement method selected to measure the analyte responses. Also shown are a standard keyboard 1202 and mouse 1203. Apparatus 1200 can also contains a variety of typical computer components inside computer system. These components can include a system bus 1204, one or more disk drives 1205, RAM 1206, and a processor 1207. FIG. 12 also shows a monitor 1208 that allows information to be displayed to a user of the system. Other components can also be present depending on the exact nature of the embodiment. In various embodiments, the apparatus can include any of the features of computer system 1200.

In one embodiment, a sample is placed in the analyte measurement module 1201 where the sample is further processed and the analyte responses in the sample are measured. This information is then transferred into the computer system along a system bus 1204, and an appropriate conversion method is applied to the analyte response data using the processor 1207. The instructions the processor 1207 executes to implement instructions for any methods described herein, where the instruction can be stored on a computer readable medium such as the RAM 1206 or disk drive 1205. The results from the methods can then be displayed on the monitor 1208. Alternative embodiments can output results using other communications means. For example, the computer system could print the measured ratio using a printer or send the measured ratio to another computer over a network.

The specific details of particular embodiments may be combined in any suitable manner without departing from the spirit and scope of embodiments. However, other embodiments may be directed to specific embodiments relating to each individual aspect, or specific combinations of these individual aspects.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

The above description of exemplary embodiments has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method of analyzing a quality control (QC) strategy for an instrument used to measure an analyte in patient biological samples, the method comprising:

obtaining, by a computer system, a non-failure probability of error $P_E(0)$ of the instrument for the analyte and an average number of patient results reported between failures (MPBF) of the instrument;

obtaining, by the computer system, information of the QC strategy, including:

an interval between QC events that monitor the instrument using a reference sample; and a number of reference samples tested at each quality control event;

calculating, by the computer system, an expected number of unreliable final results $E(N_{uf})$ for the QC strategy;

obtaining, by the computer system, a probability $P_{h|u}$ that an unreliable final result leads to patient harm;

computing, by the computer system, a proportion of patient results that are incorrect due to a failure of the instrument, the proportion including $E(N_{uf})$ divided by MPBF;

computing, by the computer system, a combined probability of incorrect results by adding $P_E(0)$ and the proportion;

computing, by the computer system, a predicted probability of harm by multiplying the combined probability and the probability $P_{h|u}$;

outputting, by the computer system, an assessment of the predicted probability of harm compared to an acceptable probability of harm, wherein the acceptable probability of harm is dependent on a severity of harm resulting from an incorrect result;

in response to the assessment indicating that the predicted probability of harm is lower or greater than the acceptable probability of harm, modifying the QC strategy by modifying the interval between QC events, the number of reference samples tested at each QC event, or both; and conducting the QC events on the instrument according to the modified QC strategy.

2. The method of claim 1, wherein the assessment comprises a patient risk management index that includes the predicted probability of harm divided by the acceptable probability of harm.

3. The method of claim 2, further comprising:
determining that the QC strategy is acceptable when the patient risk management index is less than or equal to one.

4. The method of claim 2, further comprising:
in response to determining that the patient risk management index is greater than one, modifying at least one of: the interval and the number of reference samples tested at each quality control event.

5. The method of claim 1, wherein the non-failure probability of error $P_E(0)$ of the instrument for the analyte includes:
a contribution from a statistical variance of different measurements of samples; and
a contribution from a quality specification of the instrument for the analyte.

6. The method of claim 1, further comprising:
determining $E(N_{uf})$ in terms of a systematic error (SE) of the instrument;
obtaining a probability distribution for a range of values of SE; and
calculating $E(N_{uf})$ by computing an integral of $E(N_{uf})$ with respect to the probability distribution on the range of values of SE.

7. The method of claim 1, wherein the predicted probability of harm, $P_H$, is computed as the value of $\{P_E(0)+E(N_{uf})/MPBF\} \cdot P_{h|u}$.

8. A method of selecting parameters for a quality control (QC) strategy for an instrument used to measure an analyte in patient biological samples, the method comprising:
obtaining, by a computer system, a non-failure probability of error $P_E(0)$ of the instrument for the analyte, an average number of patient results reported between failures (MPBF) of the instrument, and a severity of harm;
obtaining, by the computer system, a probability $P_{h|u}$ that an unreliable final result leads to patient harm;
using the severity of harm to determine a maximum acceptable probability of harm, $MaxP_H$;
calculating a maximum allowable expected number of unreliable final patient results due to test system failure, $E(N_{uf})_{ALLOWABLE}$ using at least $MaxP_H$;
selecting values of user-selectable parameters of the QC strategy so that, with the selected values, the QC strategy has a resulting value of $E(N_{uf})$ that is less than or equal to $E(N_{uf})_{ALLOWABLE}$; and
conducting quality control events on the instrument according to the QC strategy.

9. The method of claim 8 wherein $E(N_{uf})_{ALLOWABLE}$ is calculated by:
computing a ratio comprising $MaxP_H$ divided by $P_{h|u}$;
computing a difference value by subtracting $P_E(0)$ from the ratio; and
multiplying the difference value by MPBF.

10. The method of claim 8, wherein $MaxP_H$ is determined from the severity of harm by obtaining a maximum acceptable probability of harm corresponding to the severity of harm.

11. The method of claim 10, wherein the maximum acceptable probability of harm is expressed as a number of occurrences within a time period.

12. The method of claim 10, wherein the maximum acceptable probability of harm is the maximum value of a numerical interval.

13. The method of claim 8, wherein the user-selectable parameters of the QC strategy include a number of patient samples of an interval between QC events that monitor the instrument using a reference sample and a number of reference samples tested at each quality control event.

14. A computer product comprising a non-transitory computer readable medium storing a plurality of instructions for controlling a computer system to perform a method of analyzing a quality control (QC) strategy for an instrument used to measure an analyte in patient biological samples, the method comprising:
obtaining, by the computer system, a non-failure probability of error $P_E(0)$ of the instrument for the analyte and an average number of patient results reported between failures (MPBF) of the instrument;
obtaining, by the computer system, information of the QC strategy, including:
an interval between QC events that monitor the instrument using a reference sample; and
a number of reference samples tested at each quality control event;
calculating, by the computer system, an expected number of unreliable final results $E(N_{uf})$ for the QC strategy;
obtaining, by the computer system, a probability $P_{h|u}$ that an unreliable final result leads to patient harm;
computing, by the computer system, a proportion of patient results that are incorrect due to a failure of the instrument, the proportion including $E(N_{uf})$ divided by MPBF;
computing, by the computer system, a combined probability of incorrect results by adding $P_E(0)$ and the proportion;
computing, by the computer system, a predicted probability of harm by multiplying the combined probability and the probability $P_{h|u}$;
outputting, by the computer system, an assessment of the predicted probability of harm compared to an acceptable probability of harm, wherein the acceptable probability of harm is dependent on a severity of harm resulting from an incorrect result; and
in response to the assessment indicating that the predicted probability of harm is lower or greater than the acceptable probability of harm, modifying the QC strategy by modifying the interval between QC events, the number of reference samples tested at each QC event, or both; and conducting the QC events on the instrument according to the modified QC strategy.

15. The computer product of claim 14, wherein the assessment comprises a patient risk management index that includes the predicted probability of harm divided by the acceptable probability of harm.

16. The computer product of claim 15, wherein the method further comprises:
determining that the QC strategy is acceptable when the patient risk management index is less than or equal to one.

17. The computer product of claim 15, wherein the method further comprises:
in response to determining that the patient risk management index is greater than one, modifying at least one of: the interval and the number of reference samples tested at each quality control event.

18. The computer product of claim 14, wherein the non-failure probability of error $P_E(0)$ of the instrument for the analyte includes:
a contribution from a statistical variance of different measurements of samples; and
a contribution from a quality specification of the instrument for the analyte.

19. The computer product of claim 14, wherein the method further comprises:
determining $E(N_{uf})$ in terms of a systematic error (SE) of the instrument;
obtaining a probability distribution for a range of values of SE; and
calculating $E(N_{uf})$ by computing an integral of $E(N_{uf})$ with respect to the probability distribution on the range of values of SE.

20. The computer product of claim 14, wherein the predicted probability of harm, $P_H$, is computed as the value of $\{P_E(0)+E(N_{uf})/MPBF\} \cdot P_{h|u}$.

21. A computer product comprising a non-transitory computer readable medium storing a plurality of instructions for controlling a computer system to select parameters for a quality control (QC) strategy for an instrument used to measure an analyte in patient biological samples, the method comprising:

obtaining, by a computer system, a non-failure probability of error $P_E(0)$ of the instrument for the analyte, an average number of patient results reported between failures (MPBF) of the instrument, and a severity of harm;
obtaining, by the computer system, a probability $P_{h|u}$ that an unreliable final result leads to patient harm;
using the severity of harm to determine a maximum acceptable probability of harm, $MaxP_H$;
calculating a maximum allowable expected number of unreliable final patient results due to test system failure, $E(N_{uf})_{ALLOWABLE}$ using at least $MaxP_H$;
selecting values of user-selectable parameters of the QC strategy so that, with the selected values, the QC strategy has a resulting value of $E(N_{uf})$ that is less than or equal to $E(N_{uf})_{ALLOWABLE}$; and
conducting quality control events on the instrument according to the QC strategy.

22. The computer product of claim 21, wherein $E(N_{uf})_{ALLOWABLE}$ is calculated by:
computing a ratio comprising $MaxP_H$ divided by $P_{h|u}$;
computing a difference value by subtracting $P_E(0)$ from the ratio; and
multiplying the difference value by MPBF.

23. The computer product of claim 21, wherein $MaxP_H$ is determined from the severity of harm by obtaining a maximum acceptable probability of harm corresponding to the severity of harm.

24. The computer product of claim 23, wherein the maximum acceptable probability of harm is expressed as a number of occurrences within a time period.

25. The computer product of claim 23, wherein the maximum acceptable probability of harm is the maximum value of a numerical interval.

26. The computer product of claim 21, wherein the user-selectable parameters of the QC strategy include a number of patient samples of an interval between QC events that monitor the instrument using a reference sample and a number of reference samples tested at each quality control event.

* * * * *